United States Patent
Pescher et al.

(10) Patent No.: US 7,780,859 B2
(45) Date of Patent: *Aug. 24, 2010

(54) UNCOUPLING AGENTS

(75) Inventors: Yvette Pescher, Paris (FR); Robert Eric Talbot, Cannock (GB); Luc Olivier Louvel, Lyons (FR); Agnes Pilas-Begue, Miribel (FR); Laetitia Catinon, Saint Julien (FR); Gilles Michael Moreau, Sainte Consorce (FR)

(73) Assignee: Rhodia Operations, Aubervilliers (FR)

( * ) Notice: Subject to any disclaimer, the term of this patent is extended or adjusted under 35 U.S.C. 154(b) by 812 days.

This patent is subject to a terminal disclaimer.

(21) Appl. No.: 10/559,970

(22) PCT Filed: Jun. 21, 2004

(86) PCT No.: PCT/GB2004/002656

§ 371 (c)(1),
(2), (4) Date: Sep. 14, 2006

(87) PCT Pub. No.: WO2004/113236

PCT Pub. Date: Dec. 29, 2004

(65) Prior Publication Data
US 2007/0095763 A1    May 3, 2007

(30) Foreign Application Priority Data
Jun. 20, 2003 (GB) ................. 0314365.8
Dec. 6, 2003 (GB) ................. 0328388.4

(51) Int. Cl.
*C02F 1/50*    (2006.01)

(52) U.S. Cl. ............ 210/764; 210/631; 210/699; 210/755; 422/15; 422/28

(58) Field of Classification Search ............... 210/764
See application file for complete search history.

(56) References Cited

U.S. PATENT DOCUMENTS 4,673,509 A  *  6/1987  Davis et al. ............... 210/699
4,966,716 A  *  10/1990  Favstritsky et al. ...... 210/764
5,385,896 A  *  1/1995  Bryan et al. ............. 514/129

(Continued)

FOREIGN PATENT DOCUMENTS

EP    1 080 641    3/2001

(Continued)

OTHER PUBLICATIONS

International Search Report, International Application No. PCT/GB2004/002656 dated Dec. 4, 2004.

*Primary Examiner*—Peter A Hruskoci
(74) *Attorney, Agent, or Firm*—Buchanan Ingersoll & Rooney PC

(57) ABSTRACT

The invention provides the use of a water-soluble biocide as an uncoupling agent at an effective amount to control bacterial biomass in an aqueous system. The invention also provides a method for controlling the growth of bacterial biomass in an aqueous system. The method comprises adding to, or contacting with, the aqueous system an effective amount of an uncoupling agent which is a water-soluble biocide. In a preferred embodiment the method comprises contacting an effective amount of an uncoupling agent which is a water-soluble biocide directly with the bacterial biomass in an aqueous system.

22 Claims, 4 Drawing Sheets

U.S. PATENT DOCUMENTS

| | | | |
|---|---|---|---|
| 5,422,015 A * | 6/1995 | Angell et al. | 588/257 |
| 5,536,410 A * | 7/1996 | Kitatsuji et al. | 210/626 |
| 5,599,461 A * | 2/1997 | Peltier et al. | 210/764 |
| 5,670,055 A * | 9/1997 | Yu et al. | 210/698 |
| 5,741,757 A * | 4/1998 | Cooper et al. | 504/153 |
| 6,001,158 A * | 12/1999 | Elphingstone et al. | 106/18.31 |
| 6,165,364 A * | 12/2000 | Maunuksela et al. | 210/631 |
| 6,784,168 B1 * | 8/2004 | Jones et al. | 514/76 |
| 7,214,292 B2 * | 5/2007 | Bowdery et al. | 162/78 |
| 7,407,590 B2 * | 8/2008 | Ludensky et al. | 210/698 |

FOREIGN PATENT DOCUMENTS

| | | |
|---|---|---|
| GB | 1 221 550 | 2/1971 |
| WO | WO 99/33345 | 7/1999 |

* cited by examiner

UNCOUPLING AGENTS

This application is an application under 35 U.S.C. Section 371 of International Application Number PCT/GB2004/002656 filed on Jun. 21, 2004.

This invention relates to uncoupling agents for use in the control of bacterial biomass in aqueous systems, to the use of such agents and to a method of using such agents.

Mechanistically, the generation of biomass in wastewater treatment arises from the consumption of nutrients in the wastewater. By a process of respiration, the nutrients are oxidised and this releases energy, which can be used by the microorganisms in cell division. If this energy could be "wasted", this would result in a reduced generation of biomass by inhibition of energy production Bacterial biomass produced during the treatment of wastewater is costly to dispose of and so a reduction in biomass leads to reduced disposal costs.

Details of the biochemistry and mechanisms involved in cell respiration are given in, for example, "Biochemistry", $3^{rd}$ edition, author: Lubert Stryer, publisher: W.H. Freemen & Company, New York 1988. Also in "General Microbiology", $3^{rd}$ edition, authors: Roger Y. Stanier, Michael Doudoroff and Edward A. Adelberg, publisher: Macmillan, 1971. For the purposes of this patent application, the important point to note is that consumption of nutrients causes a proton flux which, in another part of the cell, is used to create adenosine triphosphate (ATP), via oxidative phosphorylation. ATP provides the energy for cell processes including cell division.

Hitherto, certain organic chemical compounds have been identified in the laboratory that will act as "uncoupling agents" to disrupt the proton flux. This results in a reduction in bacterial cell division by uncoupling the proton flux thus reducing the energy available to the bacteria. The wasted energy appears as heat. The use of uncoupling agents can often cause increased nutrient consumption (which is desirable) due to the loss of respiratory control. However, the aforementioned uncoupling agents are usually phenolic compounds, e.g. 2,4-dinitrophenol and para-nitrophenol; halogenated products, e.g. carbonylcyanide-p-trifluoromethoxyphenylhydrazone and 2,4,5-trichlorophenol or nitro compounds. All are unsuitable for use in aqueous systems due to their high environmental toxicity.

Accordingly the present invention provides the use of a water-soluble biocide as an uncoupling agent at an effective amount to control bacterial biomass in an aqueous system.

The effective amount of the water-soluble biocide added to the aqueous system is up to 5000 mg/l, for example up to 3000 mg/l, such as up to 1000 mg/l. Preferably, the effective amount of the water-soluble biocide added to the aqueous system is from 0.005 mg/l to 500 mg/l, for example from 0.01 mg/l to 300 mg/l, such as from 0.05 mg/l to 100 mg/l. More preferably, the effective amount of water-soluble biocide is from 0.1 to 10 mg/l, for example from 0.5 mg/l to 7.5 mg/l, such as from 1 to 5 mg/l.

Alternatively, the effective amount of said water-soluble biocide may be from 0.1 to 10,000 milligrams per gram of sludge solids in the aqueous system. Preferably, from 0.5 to 1000 mg/g, for example, from 1 to 500 mg/g, such as from 5 to 100 mg/g.

In a preferred embodiment the current invention provides the use of a water-soluble biocide as an uncoupling agent, the water-soluble biocide comprising an alkyl-substituted phosphonium compound of formula (I), an alkyl-substituted phosphine of formula (II) and a condensate of formula (III):

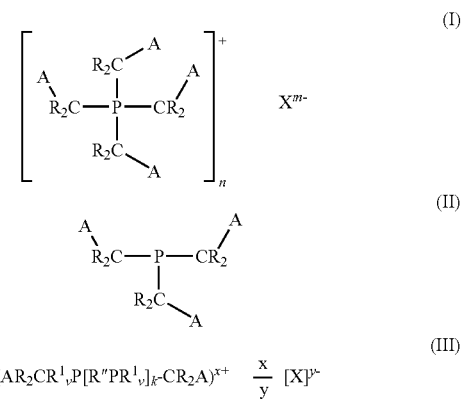

wherein:

X is an anion;

n is the valency of X represented by m;

each A can be the same or different and is selected from OH, OR, $SO_3R$, $PO_3R_2$, COOH, COOR, $SO_3H$, $PO_3H_2$, $CH_2COOH$, substituted alkyl, aryl and substituted amino groups;

each R, and each R, when present, in each A group, is independently selected from hydrogen, a $C_1$ to $C_{20}$ alkyl, aryl, substituted alkyl or aryl, carboxy or carboxy ester; wherein each $CR_2$ group may be the same or different;

R" is a divalent hydrocarbon radical having from 2-20 carbon atoms and is optionally substituted with one or more substituents selected from the group consisting of halogen, hydroxy, carboxy, amino, alkylamino, or $PR^1_mCH_2OH$ groups or interrupted by one or more ether or carbonyl linkages;

each $R^1$ is independently a monovalent hydrocarbon radical having from 1 to 25 carbon atoms and optionally substituted with one or more substituents selected from the group consisting of halogen, hydroxy, carboxy, amino, alkylamino, or $PR^1_vCH_2OH$ groups or interrupted by one or more ether or carbonyl linkages; and in formula (III) each v is 1 or 2, k is from 0 to 10 (e.g. from 1 to 10), x is the number of groups in the molecule having v=2 and X is a compatible anion of valency y such that the compound is water-soluble.

X is preferably selected from the group consisting of chloride, sulphate, phosphate, acetate and bromide.

The alkyl-substituted phosphonium compound is preferably tetrakis(hydroxymethyl)phosphonium sulphate. Alternatively, the alkyl-substituted phosphonium compound may be selected from the group consisting of tetrakis(hydroxymethyl)phosphonium chloride, tetrakis(hydroxymethyl)phosphonium bromide and tetrakis(hydroxymethyl)phosphonium phosphate.

The condensate is preferably a condensate of tris(hydroxyorgano)phosphine with a nitrogen containing compound.

The nitrogen containing compound is preferably urea. Alternatively the nitrogen containing compound is selected from a $C_{1-20}$ alkylamine, dicyandiamide, thiourea and guanidine Alternatively the invention provides the use as an uncoupling agent a water-soluble biocide that comprises a compound selected from the following:

quaternary ammonium compounds, e.g. dodecyl trimethyl ammonium chloride, cetyltrimethylammonium bromide, benzalkonium chloride, didecyldimethylammonium chloride and alkyldimethylbenzylammonium chloride;

polymeric quaternary ammonium compounds, e.g. polyoxyethylene (dimethylimino)ethylene dichloride;

polymeric biguanide hydrochlorides, e.g. polyhexamethylenebiguanide hydrochloride, dodecylguanidine hydrochloride;

tris(hydroxymethyl)nitromethane;

4,4-dimethylozazolidine;

phenoxypropanol;

phenoxyethanol;

glyoxal;

acrolein;

aldehydes, e.g. formaldehyde, glutaraldehyde;

triazines, e.g. 1,3,5-tris(2-hydroxyethyl)-1,3,5-hexahydrotriazine;

quaternary phosphonium compounds, e.g. tributyltetradecylphosphonium chloride and tetradecyl tributyl phosphonium chloride;

2-bromo-4-hydroxyacetophenone;

carbamates, e.g. sodium N-dimethyldithiocarbamate, disodium ethylene bisdithiocarbamate;

tertbuthylazine;

tetrachloro-2,4,6-cyano-3-benzonitrile;

thiazole and isothiazole derivatives such as 2-methyl-4-isothiazolin-3-one, 5-chloro-2-methyl-4-isothiazolin-3-one, 5-chloro-2-methyl-3(2H)-isothiazolone and 1,2-benzisothiazolin-3-one;

compounds with activated halogen groups such as 2-bromo-2-nitro-propan-1,3-diol and 2,2-dibromo-3-nitrilopropionamide.

bis chloromethyl sulphone, and methylene bis thiocyanate.

The water-soluble biocide for use as an uncoupling agent may be formulated with one or more of the following chemicals conventionally used in wastewater treatment:

a surfactant;

an antifoam;

a scale inhibitor;

a corrosion inhibitor;

a biocide;

a flocculant;

a dewatering aid, and a dispersant.

Preferably, the aqueous system will be a wastewater treatment plant that is used for the treatment of industrial or municipal effluent. Such a plant typically takes in wastewater from industrial processes (e.g. paper production, food processing, chemical industry) and/or domestic and institutional habitations and the like and, by using micro-organisms in aerobic, anoxic (e.g. denitrification) and/or anaerobic processes, to consume organic contaminants and render the water fit for re-use or discharge into the environment.

The present invention also provides the use as an uncoupling agent of conventional, water-soluble, water treatment biocides as defined above.

The present invention further provides an uncoupling agent comprising one or more conventional water-soluble, water treatment biocide(s) as defined above.

The present invention further provides a method for controlling the growth of bacterial biomass in an aqueous system comprising adding to, or contacting with, the aqueous system an effective amount of an uncoupling agent which is a water-soluble biocide as defined above.

In a preferred embodiment the present invention provides a method for controlling the growth of bacterial biomass in an aqueous system, which method comprises contacting an effective amount of an uncoupling agent which is a water-soluble biocide as defined above directly with the bacterial biomass.

The effective amount of the water-soluble biocide added to the aqueous system is up to 5000 mg/l, for example up to 3000 mg/l, such as up to 1000 mg/l. Preferably, the effective amount of the water-soluble biocide added to the aqueous system is from 0.005 mg/l to 500 mg/l, for example from 0.01 mg/l to 300 mg/l, such as from 0.05 mg/l to 100 mg/l. More preferably, the effective amount of water-soluble biocide is from 0.1 to 10 mg/l, for example from 0.5 mg/l to 7.5 mg/l, such as from 1 to 5 mg/l. Alternatively, the effective amount of said water-soluble biocide may be from 0.1 to 10,000 milligrams per gram of sludge solids in the aqueous system. Preferably, from 0.5 to 1000 mg/g, for example, from 1 to 500 mg/g, such as from 5 to 100 mg/g.

Contacting the bacterial biomass with the water-soluble biocide directly has been found to lead to improved efficiency of the uncoupling agent in controlling bacterial biomass. The direct contact of the water-soluble biocide with bacterial biomass is termed "flash dosing" or "flash mixing". It has been found that if the uncoupling agent is simply added directly to a bioreactor containing sludge then the efficacy of the agent is substantially reduced as the uncoupling agent is able to interact with other matter in the bioreactor and the action of the water-soluble biocide is substantially reduced.

The invention will now be described merely by way of example with reference to the following examples and accompanying figures, of which:

Figure 1:
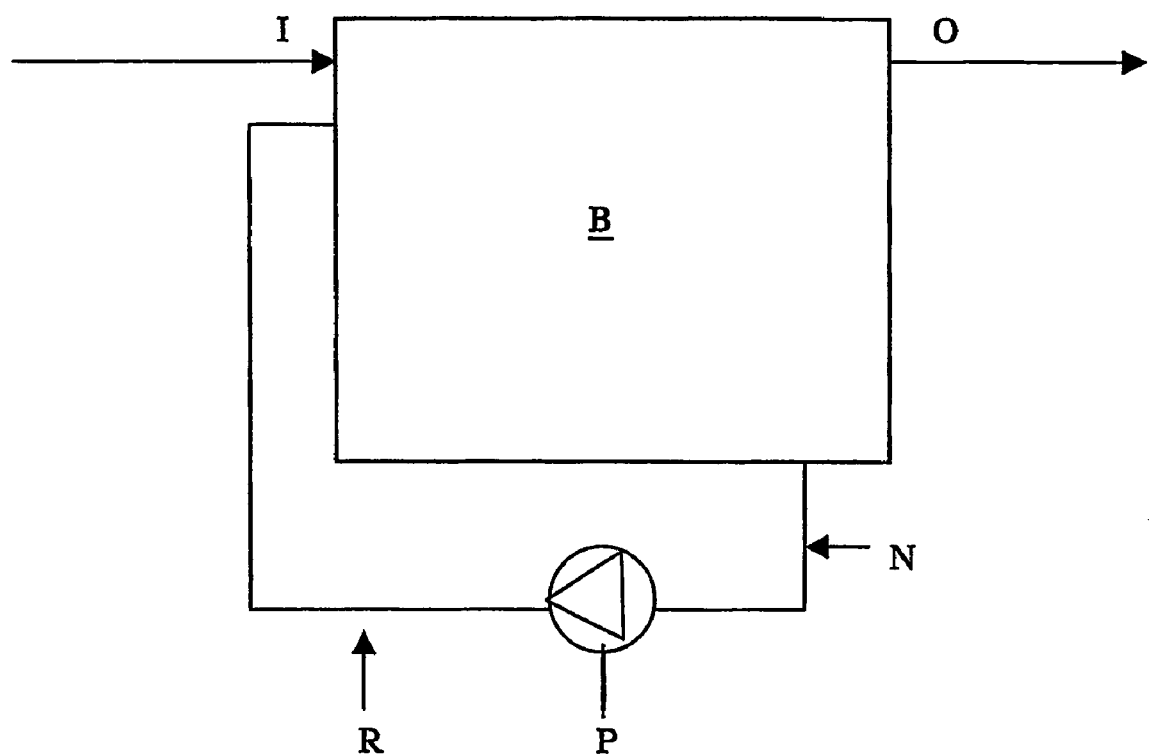
FIG. 1 is a diagram illustrating the process of flash mixing.

Referring to FIG. 1 a typical bioreactor B is shown with a recirculating line R into which the water-soluble biocide is injected. The bioreactor contains sludge, which is essentially a mass of typical wastewater treatment microorganisms such as bacteria, protozoa, worms and fungi. The bioreactor B has an inlet I for wastewater and an outlet O for treated water. The sludge is extracted from the bioreactor into the recirculation line R by means of a pump P. Typically, a peristaltic pump is used. The candidate water-soluble biocide is introduced to the sludge in the recirculating line via a needle connected to a syringe pump N. It will be appreciated that in a commercial scale bioreactor the water-soluble biocide will be introduced via a tee-junction or an injection quill and a progressive cavity pump may replace the peristaltic pump. This enables direct contact of the sludge with the water-soluble biocide. The water-soluble biocide may be introduced into the recirculation line R at a location behind or ahead of the pump P.

However, it will be appreciated that the implementation of the invention is not restricted to using the method of "flash mixing" and other dosing methods may be used if so desired.

EXAMPLE 1

Semi-Continuous Pilot Study with Flash Mixing

1. Equipment

Figure 2:
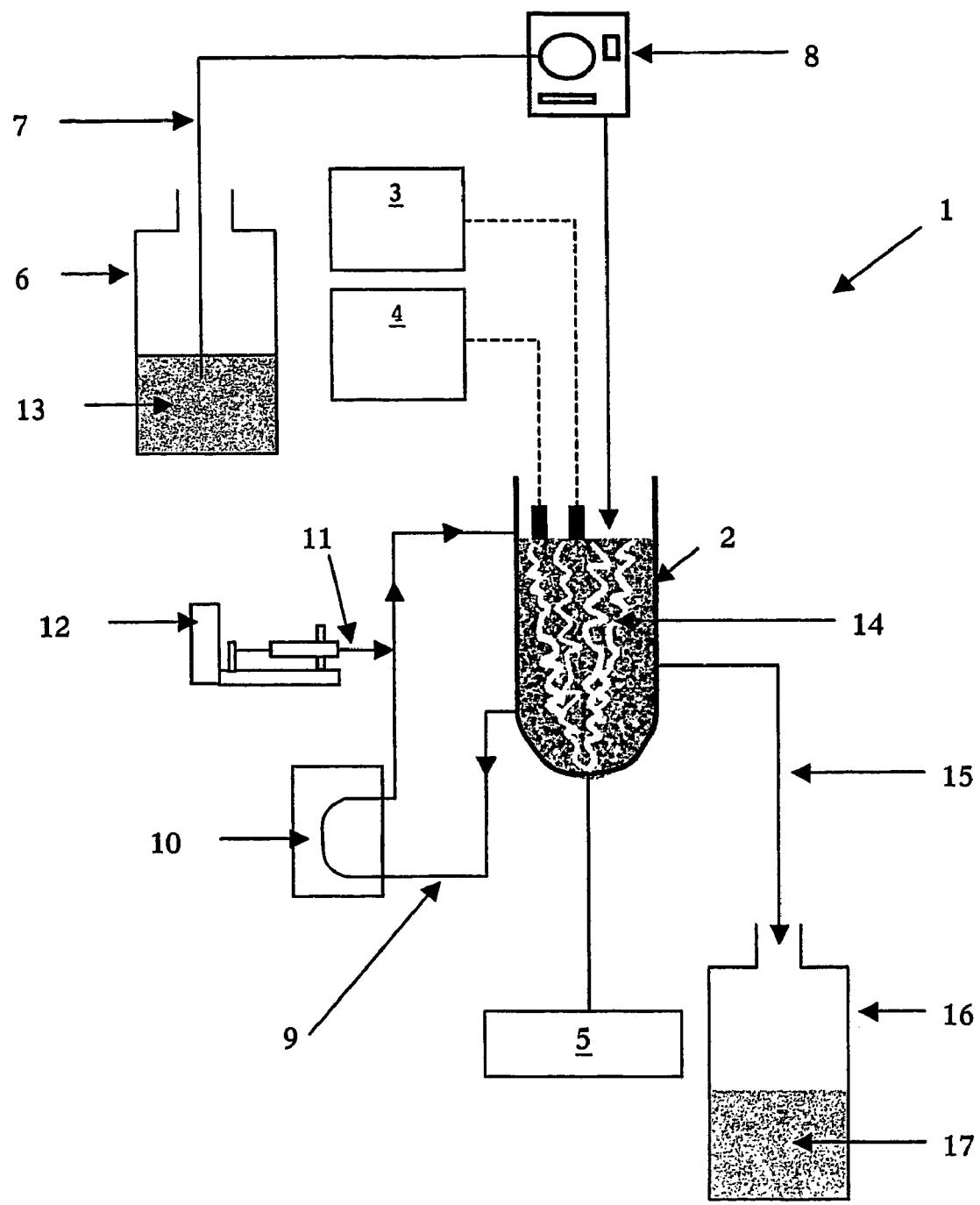
FIG. 2 is a diagram of a semi-continuous chemostat reactor system used in the present invention.

A series of semi-continuous chemostat reactors was constructed to simulate wastewater treatment processes. The arrangement of a semi-continuous chemostat reactor is shown in FIG. 2.

The central part of the equipment is the biological chemostat reactor 1. The reactor vessel 2 is made of glass, with an internal volume of 10 liters and is fitted with pH 3 and dissolved oxygen 4 sensors and an air sparge 5. This contains the sludge, which is, essentially, a mass of typical wastewater treatment microorganisms. The reactor operates at an ambient temperature (approximately 20° C.).

Simulated wastewater 13 is contained in a separate vessel 6 and maintained at 4° C. to prevent microbial spoilage. It is transferred into the reactor via a supply line 7 and a peristaltic pump 8.

A recirculating line 9 is provided on the reactor comprising a length of flexible silicone tubing and a peristaltic pump 10. The peristaltic pump extracts the sludge from the reactor into the recirculation line. The candidate water-soluble biocide is introduced into this line 9 through a needle 11, which is fed by a syringe pump 12. Using this system it is possible to achieve "flash mixing" which ensures rapid contact of the water-soluble biocide with the sludge microorganisms. The internal diameter of the recirculating line was 8 mm and the flow velocity was 0.5 meters per second, which gave a contact time, between candidate water-soluble biocide and sludge of 3 seconds before it re-entered the reactor.

Treated effluent 17 is removed from the reactor into a collecting vessel 16 via an outlet line 15.

2. Procedure

The reactor was charged with sludge obtained from the Municipal wastewater treatment works at Courly-Lyon, in France. This sludge provided the "seed" to start the process off. The reactor was then filled, to the 5 liter mark, with simulated wastewater, adjusted to approximately pH 7.5, and aeration was commenced. The reactor was continuously fed, at a rate of 800 ml per day, with simulated wastewater made to the recipe shown in Table B.

Each weekday (i.e. 5 times per week), 13.3% of the bioreactor contents were withdrawn to maintain the equilibrium. This ensured a sludge age in the region of 7.5 days.

Also, each weekday, after the adjustments described in the preceding paragraph, candidate water-soluble biocide (as a dilute solution) was injected into the system via the flash mixing recirculating line. The dilute solution was prepared by dissolving 10 grams of sodium hydrogen carbonate in approximately 900 ml of deionised water then adding 5 grams of candidate water-soluble biocide and mixing well. The mixture was then made up to 1 liter with deionised water. The appropriate volume of this dilute solution was injected to achieve the required dose level.

The experiment was conducted for 52 days before decommissioning the system.

3. Test Concentrations

Compound X was evaluated in the test. This compound is a 75% aqueous solution of tetrakis(hydroxymethyl)phosphonium sulphate (THPS). Two concentrations were evaluated: 2 and 4 milligrams per liter per day.

4. Results

TABLE A

| Treatment | Specific Activity* (g COD/g MLSS.d) | Growth Yield (g MLSS/g COD) | Growth Yield Reduction (%) |
|---|---|---|---|
| No Treatment (Control) | 0.477 | 0.272 | 0 |
| Compound X, 2 mg/l/day | 0.582 | 0.202 | 27.7 |
| Compound X, 4 mg/l/day | 0.772 | 0.167 | 37.6 |

*Specific Activity is the rate of COD removal (grams per day) divided by the quantity of sludge solids (grams) present in the reactor.

Also, the following observations were made during the pilot study:

The control (untreated) study showed a proliferation of filamentous bacteria in the sludge whereas these were substantially absent in sludge from Compound X treated systems.

There was a significantly higher concentration of protozoans and other higher organisms in the treated sludge relative to the untreated.

Compound X treatment did not impair sludge flocculation.

5. Comments

This study confirmed that Compound X flash treatment, at low dose levels, was capable of significantly reducing sludge growth whilst actually increasing the specific activity of the sludge.

Also, sludge quality was significantly improved resulting in a sludge which would flocculate more easily (in case of filamentous bacteria proliferation), thus providing operational benefits.

Simulated Wastewater Composition

TABLE B

| Component | Concentration (mg/l) |
|---|---|
| Acetic Acid | 3400 |
| Sucrose | 600 |
| Yeast Extract | 1200 |
| Casein Peptone | 600 |
| Potassium Sulphate | 180 |
| Magnesium Sulphate, heptahydrate | 180 |
| Ferrous Sulphate, heptahydrate | 30 |
| Calcium Chloride, anhydrous | 20 |
| Disodium Hydrogen | 280 |
| Sodium Hydrogen Carbonate | quantity to adjust to pH 4.3 |

EXAMPLE 2

Semi-Continuous Pilot Study with Pre-Dilution

1. Equipment

The equipment used in this test sequence was identical to that used for example 1 except that the reactor was not fitted with a recirculating line for flash mixing.

2. Procedure

The procedure was identical to that used for example 1 except that the method of dosing Compound X was different. In this case, 5 grams of Compound X was mixed into a solution containing 5 grams of sodium hydrogen carbonate in 1 liter of deionised water. 4.0 ml of this solution was added to 500 ml of clarified wastewater which had been extracted from the bioreactor. The treated clarified wastewater was then returned to the bioreactor and normal operation of the bioreactor was resumed. The final concentration of Compound X in the bioreactor therefore equates to 4 mg per liter. This procedure was conducted daily, 5 times per week.

The experiment was conducted in parallel with example 1, i.e. for 52 days before decommissioning the system.

3. Test Concentration

A Compound X concentration of 4 milligrams per liter per day was used.

4. Results

TABLE C

| Treatment | Specific Activity* (g COD/g MLSS.d) | Growth Yield (g MLSS/g COD) | Growth Yield Reduction (%) |
|---|---|---|---|
| No Treatment (Control) | 0.477 | 0.272 | 0 |
| Compound X, 4 mg/l/day | 0.636 | 0.201 | 26.4 |

*Specific Activity is the rate of COD removal (grams per day) divided by the quantity of dry sludge solids (grams) present in the reactor.

5. Comments

The reduction in growth yield in this test was only 26.4% as compared to the 37.6% reduction (see example 1), at the same dose rate, when flash mixing was used. This demonstrates the benefit of flash mixing.

EXAMPLE 3

Uncoupling by Other Water Treatment Biocides

1. Summary

A laboratory screening test was developed to determine the impact of chemical compounds on respiration parameters through an oxygen consumption pattern analysis using a model based on published work by Monod and Pirt[1]. Growth uncoupling is characterised by an increase in oxygen consumption during bacterial growth in a synthetic growth medium.

1. Monod J. 1950, Ann Inst Pasteur, "La Technique de Culture Continue, Theorie et Applications", 79:390-410. Monod J. 1942, "Recherches sur la Croissance des Cultures Bactériennes". Paris Herman p. 210. Pirt S J. (1965) "The Maintenance Energy of Bacteria In Growing Cultures". Proceedings of the Royal Society of London B 163, 224-231. "Principles of Water Quality Management". Ed: W. W. Eckenfelder, Jr. CBI Publishing Company, Inc USA. 1980 Chapter 9—Biological Waste Treatment pp 249-275.

2. Principle

Batch growth kinetic modelling and the interpretation of the oxygen consumption kinetics were implemented by mathematical modelling. Growth kinetics is described, according to Monod and Pirt's model, as follows:

$$\frac{d[X]}{dt} = a \cdot \frac{d[S]}{dt} - b \cdot [X]$$

$$\frac{d[S]}{dt} = k \cdot [X] \cdot \frac{[S]}{K_S + [S]}$$

$$\frac{d[O_2]}{dt} = a' \cdot \frac{d[S]}{dt} + b' \cdot [X]$$

[X]: Concentration in biomass amount subject to endogenous metabolism, g MLSS/L
[S]: Carbon substrate concentration, g/L
d[X]/dt: Biomass growth rate, g dry biomass/L.d
d[S]/dt: Carbon substrate consumption rate, g/L.d
a: Intrinsic substrate-biomass growth yield, g X/g substrate consumed
b: Biomass maintenance coefficient, g dry biomass/g dry biomass. d
d[$O_2$]/dt: Oxygen consumption rate, g $O_2$/L.d
a': Specific oxygen consumption coefficient, g $O_2$/g organic substrate consumed.
b': Endogenous respiration coefficient, g $O_2$/gX
k Maximum specific activity, gS/g dry biomass.d
$K_s$: Apparent substrate affinity coefficient or half maximum specific activity substrate concentration, mg/l Relationship between a and a': a'+(b'/b)*a=1

Relationship between b and b': b'=1.25*b

For the evaluation of proposed water-soluble biocides, the oxygen consumption kinetics are measured and, a process of computer iteration optimises the equation coefficients optimised to fit the oxygen consumption curve.

From the optimised coefficients, the degree of bacterial uncoupling can be calculated.

3. Equipment

Figure 3:
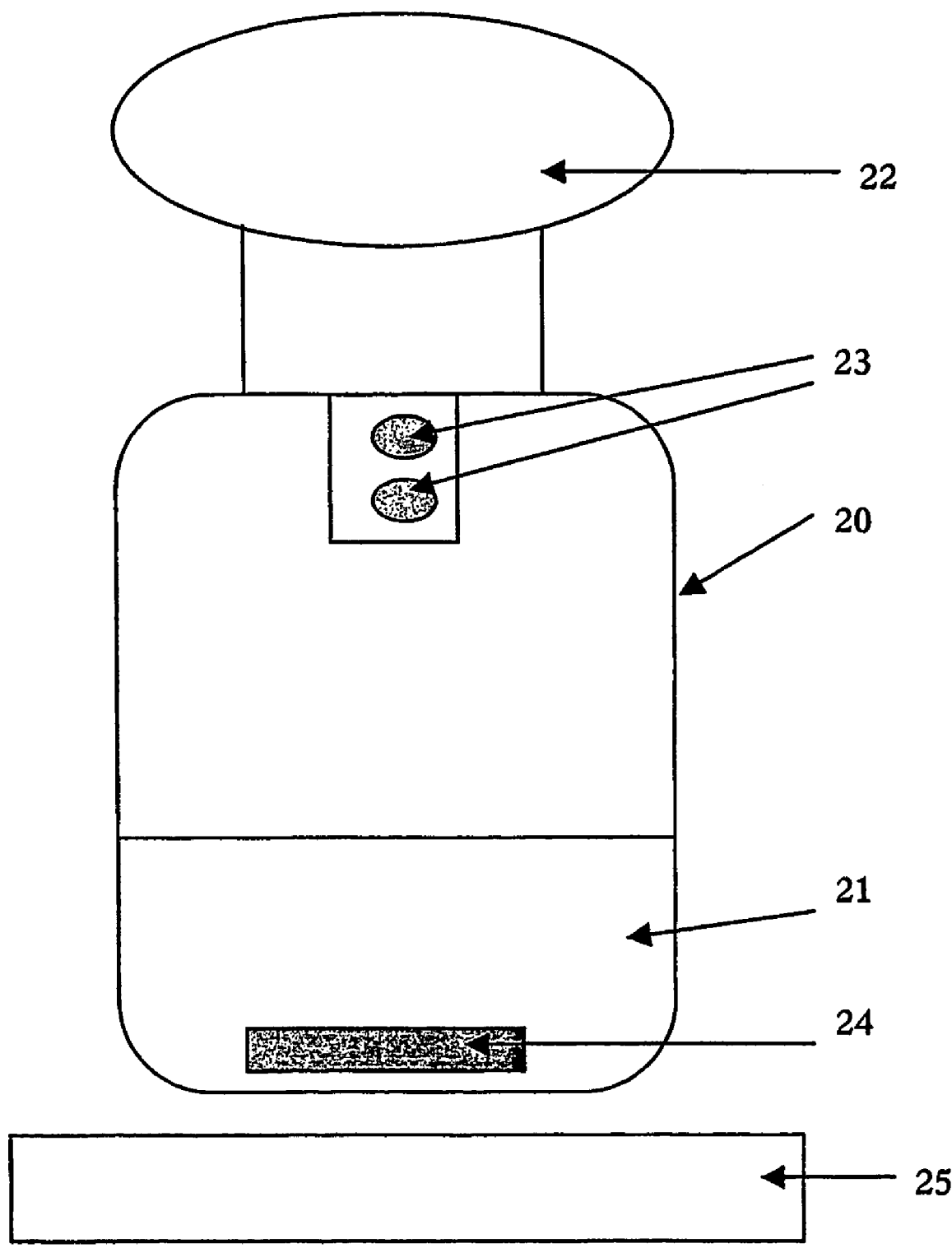
FIG. 3 is a diagram of an Oxitop® BOD system used to obtain oxygen consumption data.

An Oxitop® BOD System, supplied by Wissenschaftlich-Technische Werkstätten GmbH, Dr.-Karl-Slevost-Strasse 1, D-82362 Weilheim, Germany, was used for the screening tests (see FIG. 3). The complete system (see FIG. 3) comprised:

500 ml glass bottles 20 containing seeded culture medium 21;

Each bottle was capped with a screw-on gas pressure meter 22 capable of recording up to 360 pressure data points. Sodium hydroxide pellets 23 were incorporated into the system to absorb carbon dioxide produced during bacterial respiration.

The culture medium 21 was stirred using a magnetic stirrer 25 and a magnetic flea 24.

The bottles were housed in a temperature controlled container (20° C.)

Data acquisition was by infra-red link with a hand-held control unit.

Data was finally transferred from the hand-held control unit to an Excel® spreadsheet file for the calculations to be performed.

4. Test Biocides

Three conventional water treatment biocides were evaluated as bacterial water-soluble biocides. Each represented a major class of biocide type used conventionally in the water treatment industry. In addition, 2,4-dinitrophenol, a conventionally known bacterial water-soluble biocide was included in the test sequence for comparison. Details, as follows:

TABLE D

| Test Substance | Code | Class of biocides represented |
|---|---|---|
| 2,4 Dinitrophenol | A | — |
| Glutaraldehyde (15% active ingredient) | B | Aldehydes |
| Dodecyltrimethylammonium chloride (laboratory chemical) | C | Quaternary ammonium salts |
| Blend of 5-chloro-2-methyl-4-isothiazolin-3-one and 2-methyl-4-isothiazolin-3-one (1.5% active ingredient) | D | Isothiazolones |

5. Test Concentrations

Based on the liquid sludge, 2,4-dinitrophenol was dosed at 20 mg/l, this being the known level at which significant uncoupling would result. The test biocides were each evaluated at 1, 2.5, 5, 10 and 25 mg/l.

6. Procedure

Growth Medium:

| | |
|---|---|
| Glucose: | 500 mg/l |
| Yeast extract Difco: | 50 mg/l |
| Mineral nutrients: | as described in Standard Method ISO 9888 (Determination of ultimate aerobic biodegradability in aquatic environment) |

Medium Seeding:

50 mg/l homogenized and washed sample from municipal activated sludge treatment unit.

Incubation:

7 days at 20° C. in BOD-meter bottles (OxiTop)

The oxygen consumption was automatically determined and recorded all through the growth and decay phases (a total of 360 data points for each test substance).

Data was interpreted using a simple growth mathematical model as described above.

The determination of the model's coefficients are made through adjustment and using the statistical test $\chi^2$ to fit the model to the experimental data.

$$\chi^2 = \sum \frac{[OC_{observed} - OC_{theoretical}]^2}{OC_{theoretical}}$$

where OC is the oxygen consumption.

7. Results

Figure 4:
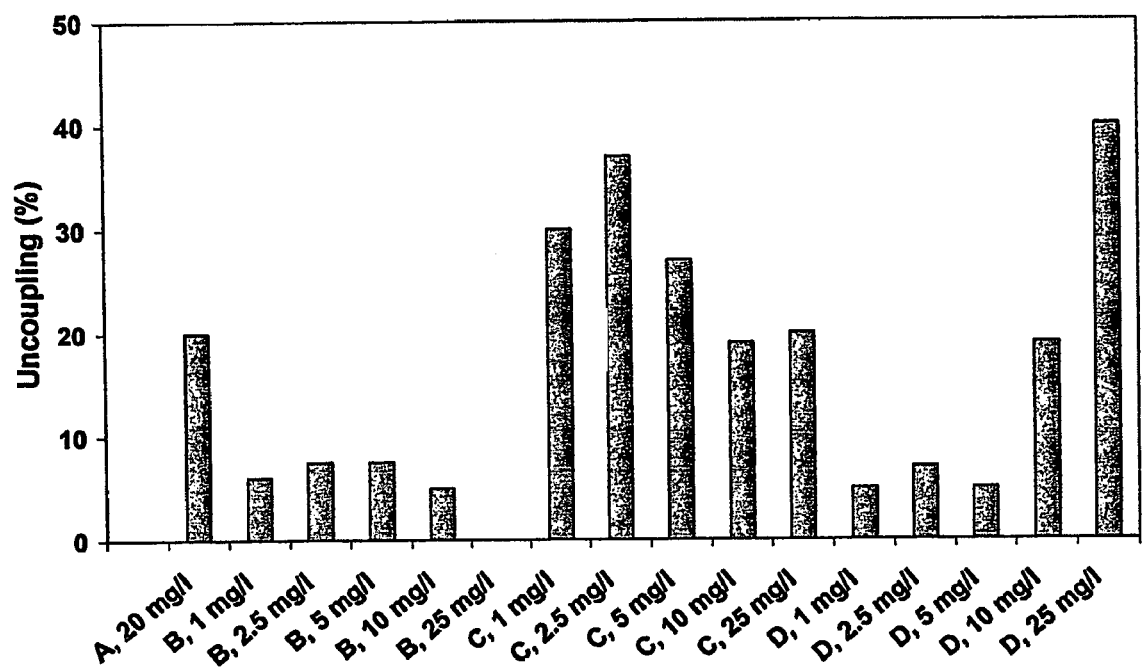
FIG. 4 is a graph showing percentage uncoupling of four uncoupling agents.

FIG. 4 summarises the results and shows that all three test biocides produced significant and useful levels of uncoupling. Two of them (biocides C and D) produced greater levels of uncoupling at significantly lower dose levels than the conventional water-soluble biocide, 2,4-dinitrophenol. However, it should be borne in mind that these were screening tests and conditions were not optimised for the individual biocides and so it is possible that biocide B might have produced greater uncoupling under more optimum conditions.

8. Comments

The results clearly show that representatives of three major water treatment biocide classes will effect significant bacterial uncoupling at low treatment levels.

The invention claimed is:

1. A method for controlling the growth of bacterial biomass in an aqueous system comprising adding to, or contacting with, the aqueous system an effective amount of an uncoupling agent which is a water-soluble biocide comprising an alkyl substituted phosphonium compound of formula (I) or an alkyl-substituted phosphine of formula (II) or a condensate of formula (III):

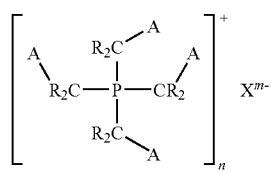

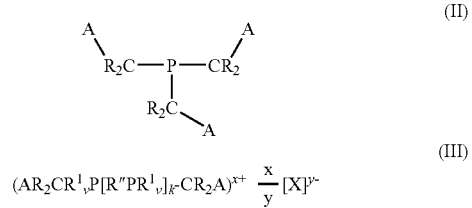

wherein:

X is an anion;

n is the valency of X represented by m;

each A can be the same or different and is selected from the group consisting of OH, OR, $SO_3R$, $PO_3R_2$, COOH, COOR, $SO_3H$, $PO_3H_2$, $CH_2COOH$, substituted alkyl, aryl and substituted amino groups;

each R, and each R in each A group, is independently selected from hydrogen, a $C_1$ to $C_{20}$ alkyl, aryl, substituted alkyl or aryl, carboxy or carboxy ester; wherein each $CR_2$ group may be the same or different, and R" is a divalent hydrocarbon radical having from 2-20 carbon atoms and is optionally substituted with one or more substituents selected from the group consisting of halogen, hydroxy, carboxy, amino, alkylamino, and $PR^1_m CH_2OH$ groups, or interrupted by one or more ether or carbonyl linkages;

each $R^1$ is independently a monovalent hydrocarbon radical having from 1 to 25 carbon atoms and optionally substituted with one or more substituents selected from the group consisting of halogen, hydroxy, carboxy, amino, alkylamino, and $PR^1_m CH_2OH$ groups, or interrupted by one or more ether or carbonyl linkages, and in formula (III) each v is 1 or 2, k is from 0 to 10, x is the number of groups in the molecule having v=2 and X is a compatible anion of valency y such that the compound is water-soluble, wherein the aqueous system is a wastewater treatment plant used for the treatment of industrial or municipal effluent, wherein said biocide reduces sludge growth in said aqueous system.

2. The method as claimed in claim 1, wherein X is selected from the group consisting of chloride, sulphate, phosphate, acetate and bromide.

3. The method as claimed in claim 1, wherein the alkyl-substituted phosphonium compound is tetrakis(hydroxymethyl)phosphonium sulphate.

4. The method as claimed in claim 1, wherein the alkyl-substituted phosphonium compound is selected from the group consisting of tetrakis(hydroxymethyl)phosphonium chloride, tetrakis(hydroxymethyl)phosphonium bromide, tetrakis(hydroxymethyl)phosphonium acetate and tetrakis(hydroxymethyl)phosphonium phosphate.

5. The method as claimed in claim 1, wherein the condensate is a condensate of tris(hydroxyorgano)phosphine with a nitrogen containing compound.

6. The method as claimed in claim 5, wherein the nitrogen containing compound is selected from the group consisting of a $C_{1-20}$ alkylamine, dicyandiamide, thiourea and guanidine.

7. The method as claimed in claim 1, wherein the method comprises the step of contacting an effective amount of a water-soluble biocide directly with the bacterial biomass.

8. The method as claimed in claim 7, wherein the effective amount of the water-soluble biocide added to the aqueous system is up to 5000 mg/l.

9. The method as claimed in claim 7, wherein the effective amount of the water-soluble biocide added to the aqueous system is from 0.005 mg/l to 500 mg/l.

10. The method as claimed in claim 9, wherein the effective amount of the water-soluble biocide added to the aqueous system is from 0.01 mg/l to 300 mg/l.

11. The method as claimed in claim 10, wherein the effective amount of the water-soluble biocide added to the aqueous system is from 0.05 mg/l to 100 mg/l.

12. The method as claimed in claim 7, wherein the effective amount of the water-soluble biocide added to the aqueous system is up to 1000 mg/l.

13. The method as claimed in claim 7, wherein the effective amount of the water-soluble biocide added to the aqueous system is from 0.1 mg/l to 10 mg/l.

14. The method as claimed in claim 13, wherein the effective amount of the water-soluble biocide added to the aqueous system is from 0.5 mg/l to 7.5 mg/l.

15. The method as claimed in claim 14, wherein the effective amount of the water-soluble biocide added to the aqueous system is from 1 mg/l to 5 mg/l.

16. The method as claimed in claim 1, wherein the effective amount of the water-soluble biocide added to the aqueous system is from 0.1 mg to 10000 mg per gram of sludge solids in the aqueous system.

17. The method as claimed in claim 16, wherein the effective amount of the water-soluble biocide added to the aqueous system is from 0.5 mg to about 1000 mg per gram of sludge solids in the aqueous system.

18. The method as claimed in claim 17, wherein the effective amount of the water-soluble biocide added to the aqueous system is from 1 mg to 500 mg per gram of sludge solids in the aqueous system.

19. The method as claimed in claim 18, wherein the effective amount of the water-soluble biocide added to the aqueous system is from 5 mg to 100 mg per gram of sludge solids in the aqueous system.

20. The method as claimed in claim 1, wherein the uncoupling agent comprises a compound selected from the group consisting of quaternary ammonium compounds; polymeric quaternary ammonium compounds; polymeric biguanide hydrochlorides; tris(hydroxymethyl)nitromethane; 4,4-dimethylozazolidine; phenoxypropanol; phenoxyethanol; glyoxal; acrolein; aldehydes; triazines; quaternary phosphonium compounds; 2-bromo-4-hydroxyacetophenone; carbamates; tertbuthylazine; tetrachloro-2,4,6-cyano-3-benzonitrile; thiazole and isothiazole derivatives; compounds with activated halogen groups; bis chloromethyl sulphone, and methylene bis thiocyanate.

21. The method as claimed in claim 1, wherein the water-soluble biocide is formulated with one or more of a surfactant; an antifoam; a scale inhibitor; a corrosion inhibitor; a biocide, a flocculant, a dewatering aid and a dispersant.

22. A method for controlling the growth of bacterial biomass in an aqueous system comprising:
adding to, or contacting with, the aqueous system an effective amount of an uncoupling agent which is a water-soluble biocide comprising an alkyl substituted phosphonium compound,
wherein the alkyl substituted phosphonium compound is selected from the group consisting of tetrakis(hydroxymethyl)phosphonium chloride, tetrakis(hydroxymethyl)phosphonium bromide, tetrakis(hydroxymethyl)phosphonium acetate, and tetrakis(hydroxymethyl)phosphonium phosphate, and
wherein the aqueous system is a wastewater treatment plant used for the treatment of industrial or municipal effluent,
wherein said biocide reduces sludge growth in said aqueous system.

* * * * *